United States Patent [19]

Udding et al.

[11] Patent Number: 5,468,891
[45] Date of Patent: Nov. 21, 1995

[54] MOLYBDENUM-CONTAINING FRICTION-REDUCING ADDITIVES

[75] Inventors: Anne C. Udding, Castricum; Peter A. Van Leeuwen, Amsterdam, both of Netherlands; Michael Pearson, Sittingbourne, England

[73] Assignee: Shell Oil Company, Houston, Tex.

[21] Appl. No.: 271,814

[22] Filed: Jul. 7, 1994

[30] Foreign Application Priority Data

Aug. 20, 1993 [EP] European Pat. Off. .............. 93306626

[51] Int. Cl.⁶ .................................................. C07F 11/00
[52] U.S. Cl. ................................................................ 556/61
[58] Field of Search ................................................ 556/61

[56] References Cited

U.S. PATENT DOCUMENTS

| | | | |
|---|---|---|---|
| 4,266,945 | 5/1981 | Karn | 44/68 |
| 4,466,901 | 8/1984 | Hunt et al. | 252/32.7 |
| 4,633,001 | 12/1986 | Cells | 556/44 |
| 4,692,256 | 9/1987 | Umemura et al. | 252/32.7 |

FOREIGN PATENT DOCUMENTS

| | | |
|---|---|---|
| 1054406A | 8/1981 | U.S.S.R. . |
| 1143767A | 6/1983 | U.S.S.R. . |

*Primary Examiner*—Porfirio Nazario-Gonzalez
*Attorney, Agent, or Firm*—Timothy J. Hadlock

[57] ABSTRACT

The invention provides molybdenum-containing complexes prepared by reacting a carboxylic acid or metal salt thereof, an amine and a source of cationic molybdenum, wherein the ratio of the number of equivalents of acid groups to the number of moles of molybdenum (eq:mol) is in the range from 1:10 to 10:1, and the ratio of the number of equivalents of acid groups to the number of moles of amine (eq:mol) is in the range from 20:1 to 1:10; a process for their preparation; lubricating oil compositions containing them; and their use as friction-reducing additives.

9 Claims, No Drawings

MOLYBDENUM-CONTAINING FRICTION-REDUCING ADDITIVES

FIELD OF THE INVENTION

The present invention relates to molybdenum-containing complexes, a process for their preparation, lubricating oil compositions containing them, and their use as friction-reducing additives.

BACKGROUND OF THE INVENTION

It is well known in the art that the properties of lubricating oils for internal combustion engines can be improved by the addition of molybdenum-containing materials having anti-wear and/or friction-reducing properties. Anti-wear materials prevent or slow down the wear that occurs between metal surfaces which are in close rubbing contact, particularly in the boundary lubrication regime where metal to metal contact occurs. They are known to work by forming a permanent film on the surface metal which protects it from wear phenomena which would otherwise lead to removal of metal, loss of performance and eventual welding together of metal parts. Friction-reducing materials act by reducing the friction between metal surfaces when they rub together, resulting in improved fuel economy. They are known to give benefit in both the hydrodynamic and boundary lubrication regimes.

These molybdenum-containing materials typically contain a source of active sulphur. In Column 1, line 53 to Column 2, line 2 of US-A-4,692,256 it is stated: "It has been considered essential that organic molybdenum compounds useful as lubricant additives should contain sulfur atoms in the molecules of the compounds. That is, it has been considered that the lubricating performance can be obtained by the formation of molybdenum disulfide on the lubricating surface by molybdenum and sulfur contained in the molecules. However, the present inventors have assumed that active sulfur atoms contained in the molecules may have undesirable effects in view of the metal corrosion and have made an earnest study in order to overcome the contraction. As a result, it has surprisingly been found that although the product obtained by the reaction between a molybdenum compound and an amino compound has no substantial performance when used alone as a lubricant additive, it exhibits extremely satisfactory lubricating performance when combined with a sulfur-containing compound". Examples of such sulphur-containing compounds are said in Column 4, lines 11 to 19 to include sulphurised fatty acids, sulphurised oils and fats, sulphurised olefins, disulphide compound such as dibenzyl sulphide, dithiocarbamate such as butylphenyl thiocarbamate disulphide, phosphorous- and sulphur-containing compounds such as tetraalkylthioperoxy phosphate, molybdenum dithiocarbamate, molybdenum dithiophosphate and zinc dithiophosphate.

US-A-4,266,945 discloses, as extreme-pressure and friction modifying additives in lubricants and fuels, molybdenum-containing compositions substantially free of Group IA and IIA metals which are prepared by reacting, at a temperature up to about 200° C., a mixture comprising (A) at least one acid of molybdenum, or salt thereof; (B) at least one phenol, or condensation product of said phenol and at least one lower aldehyde; and (C) at least one compound selected from the group consisting of (1) amines having the formula $R^1(R^2)NH$ wherein $R^1$ is an aliphatic hydrocarbon-based radical and $R^2$ is hydrogen or an aliphatic hydrocarbon-based radical; (2) condensation products of said amines with at least one lower aldehyde; and (3) salts of (1) or (2). The molybdenum-containing compositions may be used in conjunction with at least one compound containing active sulphur, e.g. a sulphurised olefin, a sulphurised mercaptan, a sulphurised phenol, or a dialkyl xanthate or carbamate.

The reagent (B) can be a phenol. The term "phenol" is defined as a compound containing a hydroxyl group bound directly to an aromatic ring and is said to include compounds having more than one hydroxyl group bound to an aromatic ring, and also alkylalkenyl phenols. No other phenols are mentioned. Preferred are phenols containing at least one alkyl substituent containing about 3 to 100 and especially about 6 to 20 carbon atoms, with monoalkylphenols being particularly preferred.

A reference to US-A-4,266,945 can be found in Column 1, lines 30 to 34 of US-A-4,466,901 which discloses a lubricating oil anti-friction additive composition prepared by reacting a phenolic compound, with a molybdenum compound, an amine compound and sulphur or a sulphur-yielding compound.

In Column 1, lines 52 to 56 of US-A-4,466,901, it is stated that molybdenum compounds produced by prior art methods including that of US-A-4,266,945 potentially suffer from either economic inefficiencies or from changing product requirements, i.e. they do not meet current environmental standards. Furthermore, in Column 2, lines 4 to 10, it is stated that whilst these molybdenum compounds can improve the characteristics of lubricating oils, they suffer the additional drawbacks in that they are often uneconomical or difficult to prepare, cannot be prepared in a batch process, and may or may not have sufficient amounts of sulphur incorporated within the additive to benefit fully from the molybdenum contained therein.

SU-A-1143767 discloses a lubricating composition containing (a) 1.5 to 1.53% w 2-mercaptobenzothiazole (anti-wear and anti-scuff additive), (b) 0.201 to 0.204% w p-hydroxyphenylene diamine (antioxidant additive), (c) 0.5 to 2% w molybdenyl chloride of the formula $MoO_2Cl_2 \cdot HL$ where HL is salicylaldehyde/2,4,6-trimethyl- aniline or salicylaldehyde/tert-butylamine (each of these being a Schiff base and therefore containing the group CH=N—), and (d) the balance being a synthetic oil based on an ester of pentaerythritol and $C_5$–$C_9$ aliphatic acids. Test data in the Table in Columns 5 and 6 of SU-A-1143767 (particularly the results for Composition 2 compared with those for Compositions 3 to 6) show that the anti-wear and anti-scuff properties of a lubricating composition containing components (a), (b) and (d) were enhanced by the addition of the molybdenyl chloride (c). There is no test data on any lubricating compositions containing components (c) and (d) only and therefore there is no suggestion of any anti-wear or friction-reducing capabilities of the molybdenyl chloride (c) per se.

SU-A-1054406 discloses a lubricating composition with improved lubricity containing, as anti-wear additive, 0.05 to 0.25% w molybdenyl chloride bis(salicylaldehyde anilinate), 0.45 to 2.25% w thioglycolic acid, and the balance being a synthetic oil based on an ester of pentaerythritol and $C_5$–$C_9$ aliphatic acids. The composition is referred to in SU-A-143767 discussed above where it is mentioned that the use of molybdenyl chloride bis(salicylaldehyde anilinate) is problematic since it can only be incorporated into the synthetic oil after it has first been dissolved in thioglycolic acid, which leads to the formation of sediment in the oil during long-term operation.

It has now surprisingly been found possible to prepare molybdenum-containing complexes from carboxylic compounds, being free of active sulphur, which show advantageous friction-reducing properties.

SUMMARY OF THE INVENTION

Therefore, in accordance with the present invention, there is provided a molybdenum-containing complex prepared by reacting a carboxylic acid or metal salt thereof, an amine and a source of cationic molybdenum, wherein the ratio of the number of equivalents of acid groups to the number of moles of molybdenum (eq:mol) is in the range from 1:10 to 10:1, and the ratio of the number of equivalents of acid groups to the number of moles of amine (eq:mol) is in the range from 20:1 to 1:10.

DETAILED DESCRIPTION OF THE PREFERRED EMBODIMENTS OF THE INVENTION

The present invention further provides a process for the preparation of a molybdenum-containing complex according to the invention which comprises reacting, optionally in the presence of an organic solvent, a carboxylic acid or metal salt thereof, an amine and a source of cationic molybdenum, wherein the ratio of the number of equivalents of acid groups to the number of moles of molybdenum (eq:mol) is in the range yfrom 1:10 to 10:1, and the ratio of the number of equivalents of acid groups to the number of moles of amine (eq:mol) is in the range from 20:1 to 1:10.

The carboxylic acid used in the present invention may be any compound containing one or more carboxyl groups. The carboxylic acid may be aliphatic or aromatic, and may contain a total of up to 400 carbon atoms, e.g. 2 to 400, preferably 2 to 200, more preferably 2 to 100, and especially 10 to 30, carbon atoms.

Examples of aliphatic carboxylic acids include $C_{10}$–$C_{20}$ alkane monocarboxylic acids, e.g. decanoic acid, dodecanoic acid, tetradecanoic acid, hexadecanoic acid, octadecanoic acid, as well as branched acids such as those sold by member companies of the Royal Dutch/Shell group under the trade mark "VERSATIC" (e.g. "VERSATIC" 10); $C_3$–$C_{10}$ alkane dicarboxylic acids, e.g. 1,3-propane- dioic acid, 1,4-butanedioic acid, 1,5-pentanedioic acid and 1,6-hexanedioic acid; and mixtures of two or more of these acids.

Further examples of aliphatic carboxylic acids are polyalkenyl derivatives of a monoethylenically unsaturated $C_4$–$C_{10}$ dicarboxylic acid material. The derivatives are known compounds or can be prepared by processes analogous to known processes. Thus, such a derivative may conveniently be prepared by mixing a polyalkene with a specified amount of a monoethylenically unsaturated $C_4$–$C_{10}$ dicarboxylic acid material and passing chlorine through the mixture, e.g. as described in GB-A-949,981. Alternatively, the derivative may be prepared by reacting thermally at an appropriate temperature the polyalkene with a specified amount of the dicarboxylic acid material, e.g. as described in GB-A-1,483,729.

The polyalkene may be a polymer or oligomer, for example of at least one $C_2$–$C_{10}$ monoolefin. Preferably the polyalkene is a polymer or oligomer of at least one $C_2$–$C_5$ monoolefin, e.g. ethylene oligomers such as $C_{14}$–$C_{18}$ alpha olefins derived from the "SHELL" (registered trade mark) Higher Olefins Process. The monoolefin is preferably a $C_3$–$C_4$ olefin and preferred polyalkenes derived therefrom include polyisobutylenes and atactic or isotactic propylene oligomers. Polyisobutylenes such as those sold by the British Petroleum Company under the trade marks "Ultravis", "Hyvis" and "Napvis" are particularly preferred for use in the present invention.

The polyalkene preferably has a number average molecular weight ($M_n$) in the range from 100 to 5,000, more preferably from 100 to 3,500, and especially from 200 to 2,500.

$C_4$–$C_{10}$ dicarboxylic acid materials (see for example US-A-4,086,251 and US-A-4,235,786) may for example be anhydrides, e.g. of $C_4$–$C_6$ dicarboxylic acids such as maleic acid, citraconic acid (methylmaleic acid), itaconic acid (methylene succinic acid) and ethylmaleic acid. The $C_4$–$C_{10}$ dicarboxylic acid material is preferably maleic anhydride.

When the $C_4$–$C_{10}$ dicarboxylic acid material is maleic anhydride, the polyalkenyl derivative will be a polyalkenyl succinic acid derivative.

Examples of aromatic carboxylic acids include benzoic acid; phthalic acid; terephthalic acid; alkyl benzoic acids, e.g. $C_1$–$C_{24}$ alkyl benzoic acids; naphthoic acids; salicylic acid; and, in particular, alkyl salicylic acids, e.g. $C_1$–$C_{24}$, preferably $C_{10}$–$C_{24}$, more preferably $C_{14}$–$C_{18}$, alkyl salicylic acids, and the corresponding dicarboxylic acids; as well as mixtures of two or more of these acids.

Preferred carboxylic acids for use in the present invention are $C_1$–$C_{24}$ alkyl salicylic acids and the corresponding dicarboxylic acids.

The carboxylic acid may be used as such or in the form of a metal salt. In the latter case, the salt is advantageously an alkali metal salt, e.g. a lithium, sodium or potassium salt, or preferably an alkaline earth metal salt, e.g. a magnesium, or preferably calcium, salt.

The metal salts may be neutral salts, i.e. those containing stoichiometrically equivalent amounts of metal and carboxylate moieties, or they may be overbased salts. In the present context, an overbased salt denotes a salt in which the basicity index (BI), defined as the equivalent ratio of total metal to metal salt (as determined by potentiometric titration), is greater than I. Detailed descriptions of overbasing processes are given in many patent specifications, for example GB-A-786,167.

The amine may be a primary, secondary or tertiary amine and may be aliphatic or aromatic.

Examples of aliphatic amines include monoamines of the general formula

$$R^1-N-R^2 \quad \quad (I)$$
$$\phantom{R^1-N-}R^3$$

in which each of $R^1$, $R^2$ and $R^3$ independently represents a hydrogen atom, an alkyl or alkenyl group, optionally substituted by a cycloalkyl group, or a cycloalkyl group optionally substituted by an alkyl or alkenyl group, provided that $R^1$, $R^2$ and $R^3$ do not simultaneously represent a hydrogen atom; and polyamines of the general formula

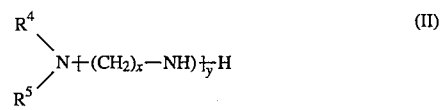

$$\begin{array}{c} R^4 \\ \phantom{R}\diagdown \\ \phantom{RR}N{+}(CH_2)_x{-}NH{\rightarrow}_y H \qquad (II)\\ \phantom{R}\diagup \\ R^5 \end{array}$$

in which each x is in the range 1 to 3, y is in the range I to IO, and $R^4$ and $R^5$ each independently represent a hydrogen atom or an alkyl group.

In this specification, unless otherwise stated, an alkyl or alkenyl group may be linear or branched and preferably contains up to 20, more preferably up to 10, and especially up to 6, carbon atoms, for example a methyl, ethyl, n-propyl, iso-propyl, n-butyl, iso-butyl, tert-butyl, n-pentyl or n-hexyl group. The substituent(s) in a substituted, branched alkyl or alkenyl group may be located either on the main chain or on the sidechain(s) of the alkyl or alkenyl group. A cycloalkyl group may contain from 3 to 8, preferably 3 to 6, carbon atoms, for example a cyclopentyl or cyclohexyl group.

Preferably in formula I above, each of $R^1$ and $R^2$ independently represents a hydrogen atom or a $C_1$–$C_6$ alkyl, especially $C_4$ alkyl, group, and $R^3$ represents a $C_1$–$C_6$ alkyl, especially $C_4$ alkyl, group. Particularly preferred monoamines of formula I are mono-, di- and tri($C_4$-alkyl)amines, such as tert-butylamine, di-n-butylamine, di-iso-butylamine and tri-nbutylamine.

In formula II above, it is preferred that each of $R^4$ and $R^5$ independently represents a hydrogen atom or a $C_1$–$C_6$ alkyl, especially methyl, group. Particularly preferred polyamines of formula II are those in which each of $R^4$ and $R^5$ independently represents a hydrogen atom or a methyl group, each x is 2 or 3 and y is in the range 1 to 6, for example 3-dimethylamino- 1-propylamine, diethylene triamine, triethylene tetramine, tetraethylene pentamine, pentaethylene hexamine and hexaethylene heptamine.

Examples of aromatic amines include aniline, imidazole and pyridine, each of which may be optionally substituted in the aromatic ring by one or more alkyl, preferably $C_1$–$C_6$ alkyl, groups.

A source of cationic molybdenum may be any material comprising molybdenum which is capable of yielding cationic molybdenum species. Examples of suitable sources include compounds of molybdenum such as oxides (e.g. molybdenum (IV) oxide—$MoO_2$, molybdenum (VI) oxide—$MoO_3$); halides (e.g. molybdenum (IV) chloride—$MoCl_4$, molybdenum (V) chloride—$MoCl_5$); acids (e.g. molybdic (VI) acid monohydrate—$H_2MoO_4.H_2O$); and salts (e.g. sodium molybdate—$Na_2MoO_4$, magnesium molybdate—$MgMoO_4$, calcium molybdate—$CaMoO_4$, ammonium dimolybdate—$(NH_4)_2Mo_2O_7$, ammonium heptamolybdate—$(NH_4)_6Mo_7O_{24}.4H_2O$). Further examples of molybdenum salts are to be found in Kirk-Othmer, "Encyclopedia of Chemical Technology", Third Edition, Vol. 15, pages 686 to 689.

Ammonium heptamolybdate is a particularly preferred source of cationic molybdenum.

The molybdenum content of the complexes of the invention may vary within wide limits. For example, the complexes may contain up to 20% w, in particular up to 15% w, molybdenum, based on the weight of the complex. Preferably, the molybdenum content is in the range from 1 to 15% w, more preferably from 2.5 to 15% w, and still more preferably from 2.5 to 13.5% w. Particularly advantageous results are obtained when the molybdenum content is in the range from 4 to 8% w, based on the weight of the complex.

The ratio of the number of equivalents of acid groups to the number of moles of molybdenum (eq:mol) is in the range from 1:10 to 10:1, preferably from 1:5 to 5:1, and especially from 1:3 to 3:1.

The ratio of the number of equivalents of acid groups to the number of moles of amine (eq:mol) is in the range from 20:1 to 1:10, preferably from 15:1 to 1:10, more preferably from 10:1 to 1:10, and especially from 10:1 to 1:5.

The number of equivalents (eq) of acid groups may be determined by multiplying the weight (in kilograms) of the sample of carboxylic acid reacted by its acid value (meq/g) as determined by titration with a base such as sodium hydroxide or potassium hydroxide.

The process of the present invention may conveniently be carried out in the presence of an organic solvent, e.g. a hydrocarbon solvent such as hexane, cyclohexane, toluene, the xylenes and mineral oils such as those sold by member companies of the Royal Dutch/Shell Group under the designations "HVI" and "XHVI" (trade mark). The reaction may conveniently be carried out at elevated temperature, i.e. above ambient temperature (20° C.), and may very conveniently be effected at the reflux temperature of the reaction mixture.

The molybdenum-containing complexes according to the present invention may be used as friction-reducing additives in lubricating oils. Accordingly, the present invention further provides a lubricating oil composition comprising a major amount of a lubricating oil and a minor amount, preferably from 0.1 to 20% w, more preferably from 0.1 to 10% w, and especially from 0.2 to 5% w, based on the total composition, of a molybdenum-containing complex according to the invention.

Suitable lubricating oils are natural, mineral or synthetic lubricating oils.

Natural lubricating oils include animal and vegetable oils, such as castor oil. Mineral oils comprise the lubricating oil fractions derived from crude oils, coal or shale, which fractions may have been subjected to certain treatments such as clay-acid, solvent or hydrogenation treatments. Synthetic lubricating oils include synthetic polymers of hydrocarbons such as polyalphaolefins; modified alkylene oxide polymers; and ester lubricants. These lubricating oils are preferably crankcase lubricating oils for spark-ignition and compression-ignition engines, but include also hydraulic lubricants, metal-working fluids and automatic transmission fluids.

Preferably the lubricating base oil component of the compositions according to the present invention is a poly-alpha- olefin oil, or a mineral lubricating oil or a mixture of mineral lubricating oils, such as those sold by member companies of the Royal Dutch/Shell Group under the designations "HVI", or "XHVI" (trade mark).

The viscosity of the lubricating base oils present in the compositions according to the present invention may vary within wide ranges, and is generally from 3 to 35mm$^1$/s at 100° C..

The lubricating oil compositions of the present invention may further contain a number of other additives such as antioxidants, metal detergents such as (overbased) alkaline earth metal phenates, sulphonates and salicylates, ashless dispersants such as polyolefinsubstituted succinimides, e.g. those described in GB-A-2,231,873, foam inhibitors, corrosion inhibitors, pour point depressants, extreme pressure/ anti-wear additives such as zinc or sodium dithiophosphates, and viscosity index improvers, e.g. linear or star-shaped polymers of a diene such as isoprene or butadiene, or a copolymer of such a diene with optionally substituted styrene. These copolymers are suitably block copolymers and are preferably hydrogenated to such an extent as to saturate most of the olefinic unsaturation.

The molybdenum-containing complex of the invention can be added separately to the lubricating oil or it can be blended with other additives and added to the lubricating oil together. A preferred method of adding the complex to the lubricating oil is first to prepare a concentrate of the complex and then to add this concentrate in a calculated, desired amount to the lubricating oil.

The present invention therefore further provides a lubricating oil concentrate comprising an inert carrier fluid and from 10 to 80% w, based on the total concentrate, of a molybdenum-containing complex according to the invention. The inert carrier fluid is conveniently a lubricating oil.

The present invention still further provides the use, as a friction-reducing additive, of a molybdenum-containing complex according to the invention.

EXAMPLES

The invention will be further understood from the following illustrative examples, in which the term "dope acid" refers to an alkyl salicylic acid composition obtained from Shell Chemicals UK, Stanlow which was purified to remove solvent components and which contained from 75 to 85% w of a mixture of $C_{14}$–$C_{18}$ alkyl salicylic acids and the corresponding diacids (the diacids being present in an amount of up to 17% w maximum), and from 15 to 25% w of a mixture of $C_{14}$–$C_{18}$ alkyl phenols.

Example 1

Preparation of a molybdenum-containing complex 50 g (120 meq; 0.12 eq) dope acid (diacid content of 9.9% w; acid value of 2.383 meq/g) were introduced into a 500 ml, three-necked, round bottom flask. To this were added 86.25 g xylene to adjust the solution to 0.88 meq/g. The flask was then fitted with an overhead stirrer and paddle, a Dean and Stark trap with condenser, and a thermometer. The stirrer was set in motion at a constant speed of 750 rpm. 15.5 g (0.12 mol) di-n-butylamine and then 14.16 g (0.0115 mol) ammonium heptamolybdate (0.08 mol Mo) were added in one portion at ambient temperature (20° C.) (ratio acid gps:Mo:amine (eq:mol:mol) of 1.5:11.5). The ammonium heptamolybdate did not dissolve and there was no noticeable rise in temperature. The reaction mixture was allowed to stir at ambient temperature for ten minutes and was then warmed to reflux (heating rate 3.2° C. per minute). The reaction mixture was heated at reflux and the water produced collected in the Dean and Stark trap. Initially, the reaction mixture was an orange-brown colour, but after thirty minutes of reflux the colour had changed to a dark bottle green. The ammonium heptamolybdate dissolved slowly over a period of two hours, aided by the addition of excess di-n-butylamine. The reaction was allowed to continue for a further four hours at reflux. Once cooled, the reaction mixture was filtered using "Hyflo" (trade mark) filter aid and the filtrate was collected. Xylene solvent was removed from the filtrate under high vacuum to yield 72.15 g of a molybdenum-containing complex as a viscous, dark bottle green oil. Analysis of the complex by Inductively Coupled Plasma Atomic Optical Spectrometry revealed a molybdenum content of 11.2% w.

Example 2

Preparation of a molybdenum/calcium-containing complex 1524.34 g (3632.5 meq; 3.633 eq) dope acid (diacid content of 9.9% w; acid value of 2.383 meq/g) were introduced into a 5 l, jacketed reaction vessel. To this were added 3018.88 g xylene to adjust the solution to 0.8 meq/g. The flask was then fitted with an overhead stirrer and paddle, a Dean and Stark trap with condenser and drying tube, and a thermometer. The stirrer was set in motion at a constant speed of 750 rpm and then 142.45 g (1.925 mol) calcium hydroxide were added to the flask in one portion. The reaction mixture was stirred for five minutes at ambient temperature (20° C.) before being heated to 100° C. (heating rate 3.2° C. per minute) and thereafter maintained at that temperature for a period of one hour.

To the cooled, orange-brown reaction mixture were added 472.65 g (3.664 mol) di-n-butylamine followed by 431.82 g (0.3507 mol) ammonium heptamolybdate (2.455 mol Mo) in one portion (ratio acid gps:Mo: amine (eq:mol:mol) of 1.5:1:1.5). On addition of these reagents, the reaction mixture became a yellow, granular suspension; there was no noticeable rise in temperature. The reaction mixture was allowed to stir at ambient temperature for ten minutes and was then heated to reflux (heating rate 3.2° C. per minute). After refluxing for six hours, the reaction mixture was cooled and filtered using "Hyflo" (trade mark) filter aid. The filtrate was collected and xylene solvent was removed from the filtrate under high vacuum to yield 1823 g of a molybdenum/calcium-containing complex as a dark brown oil. Analysis of the complex by Inductively Coupled Plasma Atomic Optical Spectrometry revealed a molybdenum content of 6.8% w and a calcium content of 2.6% w.

Examples 3 to 39

By processes similar to those described in Examples 1 and 2, further molybdenum-containing complexes according to the invention were prepared from dope acid, $C_{16}$-alkyl salicyclic acid, or a neutral calcium salt thereof, together with ammonium heptamolybdate and an amine selected from tert-butylamine, di-n-butylamine, di-iso-butylamine and tri-nbutylamine. The choice of acid/metal salt and amine used, the ratio acid gps:Mo:amine (eq:mol:mol) in each of Examples 3 to 39, as well as the percentage by weight of Mo/Ca in the final product and the yield of complex obtained in each of these examples are given in Table I below. The following abbreviations are used in Table I:

DA: dope acid

SA: C 16-alkyl salicylic acid

DA-Ca: neutral calcium salt of dope acid

SA-Ca: neutral calcium salt of $C_{16}$-alkyl salicyclic acid

TEB: tert-butylamine

DBA: di-n-butylamine

IBA: di-iso-butylamine

TBA: tri-n-butylamine

In those examples in which dope acid was used, the diacid content (% w) is given in parenthesis. 50 g samples of acid starting material were used in all except two examples, Examples 20 and 35, in which 500 g samples were used.

TABLE I

| Ex. No. | Acid Salt | Amine | Mo: amine (eq:mol:mol) | Final Product Mo (% w) | Ca (% w) | Yield (g) |
|---|---|---|---|---|---|---|
| 3 | SA | DBA | 1.2:1:1.5 | 13.3 | — | 93.2 |
| 4 | SA-Ca | DBA | 1.5:1:1 | 3.5 | 0.02 | 50.0 |
| 5 | DA (17) | DBA | 1.5:1:1 | 9.2 | — | 75.0 |
| 6 | DA (14.1) | DBA | 1.7:1:1.14 | 7.6 | — | 72.1 |
| 7 | DA (14.1) | DBA | 1.9:1:1.3 | 7.0 | — | 70.1 |
| 8 | DA (14.1) | DBA | 2.1:1:1.45 | 5.1 | — | 67.1 |
| 9 | DA (14.1) | DBA | 2.4:1:1.6 | 4.9 | — | 66.6 |
| 10 | DA (14.1) | DBA | 3:1:2 | 4.1 | — | 67.3 |
| 11 | DA (14.1) | DBA | 3:2:1 | 5.5 | — | 62.5 |

TABLE I-continued

| Ex. No. | Acid Salt | Amine | Mo: amine (eq:mol:mol) | Final Product Mo (% w) | Ca (% w) | Yield (g) |
|---|---|---|---|---|---|---|
| 12 | DA (14.1) | DBA | 3:1:1 | 4.0 | — | 58.9 |
| 13 | DA (14.1) | DBA | 1.3:1:1 | 6.4 | — | 70.1 |
| 14 | DA (14.1) | DBA | 1.2:1:1 | 7.5 | — | 77.1 |
| 15 | DA (14.1) | DBA | 1:1:1 | 7.1 | — | 57.0 |
| 16 | DA (9.9) | DBA | 1:1:1 | 10.9 | — | 52.4 |
| 17 | DA (9.9) | DBA | 1:1:1 | 12.9 | — | 53.0 |
| 18 | DA (9.9) | DBA | 1:1:1.5 | 12.7 | — | 56.5 |
| 19 | DA) (9.9) | DBA | 1:1.25:1.75 | 10.2 | — | 56.4 |
| 20 | DA (9.9) | DBA | 1:2.4:3.6 | 9.5 | — | 567.2 |
| 21 | DA (14.2) | DBA | 1:1.1:1.6 | 14.2 | — | 79.4 |
| 22 | DA (14.2) | DBA | 1.5:1:1.5 | 11.5 | — | 70.5 |
| 23 | DA (9.9) | DBA | 1.6:1:1.5 | 8.9 | — | 71.2 |
| 24 | DA (9.9) | DBA | 1.7:1:1.4 | 8.8 | — | 68.4 |
| 25 | DA (9.9) | DBA | 2:1:1.7 | 7.7 | — | 65.5 |
| 26 | DA (9.9) | DBA | 2.1:1:1.6 | 7.4 | — | 63.4 |
| 27 | DA (9.9) | DBA | 4:2.8:1 | 5.6 | — | 54.2 |
| 28* | DA (9.9) | DBA | 1.6:1:1.5 | 9.9 | — | 72.1 |
| 29 | DA (9.9) | TEB | 2:1:2 | 6.4 | — | 60.7 |
| 30 | DA (9.9) | IBA | 2:1.3:1 | 4.2 | — | 58.1 |
| 31 | DA (9.9) | IBA | 1.6:1:1.4 | 6.0 | — | 59.9 |
| 32 | DA (9.9) | TBA | 2:1.3:1 | 2.6 | — | 58.2 |
| 33 | DA (9.9) | TBA | 1.6:1:1.4 | 3.8 | — | 68.5 |
| 34* | DA (9.9) | TBA | 1.6:1:1.4 | 4.2 | — | 67.4 |
| 35 | DA-Ca (?) | DBA | 1.7:1:1 | 7.1 | 2.8 | 815.0 |
| 36 | DA-Ca (14.2) | DBA | 1.5:1:1.5 | 7.2 | 2.6 | 65.1 |
| 37 | DA-Ca (14.4) | DBA | 9.7:5:1 | 4.6 | 2.9 | 56.2 |
| 38 | DA-Ca (9.9) | DBA | 1.6:1:1.4 | 8.4 | 1.3 | 65.2 |
| 39 | DA-Ca (9.9) | DBA | 1.9:1:1.6 | 5.7 | 1.1 | 67.2 |

*reaction was carried out in the absence of any solvent

Example 40

Cam/tappet friction test rig

The friction reducing properties of the complexes obtained in Examples 1 to 3, 5 to 22, 35 and 36 were investigated by means of a cam/tappet friction test rig (CTFTR). In this test, samples of a SAE 10W/40 formulated base oil (reference base oil) were modified by the addition of varying amounts of the above complexes, and the friction properties of the resulting base oil compositions were evaluated in accordance with SAE Paper 850441, "Dynamic Friction in Cam/Tappet Lubrication" by Van Helden et al. The rig was operated at 100° C., at 800 rpm and at a load of 700N. The percentage friction reduction (FR) achieved was calculated from the following expression:

$$FR\ (\%) = \frac{u_{ref} - u_{comp}}{u_{ref}} \times 100$$

where $u_{comp}$=friction coefficient of the base oil composition
$u_{ref}$=friction coefficient of the reference base oil The results of this test are presented in Tables II and III below, in which the concentration (in parts per million—ppm) of molybdenum in each of the base oil compositions tested was calculated according to the formula:

ppm Mo=% w complex added×% w Mo in complex×100

For example, supposing a base oil composition was prepared by incorporating into a reference base oil 1.5% w of a complex having a molybdenum content of 12% w. The concentration of molybdenum in the base oil composition would be 1.5×12×100=1800 ppm

TABLE II

| Amount of Complex of Example 5 (% w) | Conc. of Mo (ppm) | Friction Coefficient | Friction Reduction (%) |
|---|---|---|---|
| 0 | 0 | 0.0819 | 0 |
| 0.3 | 275 | 0.0820 | −0.12 |
| 0.6 | 550 | 0.0801 | 2.20 |
| 0.9 | 825 | 0.0726 | 11.36 |
| 1.2 | 1100 | 0.0625 | 23.69 |
| 1.5 | 1375 | 0.0616 | 24.79 |
| 1.8 | 1650 | 0.0610 | 25.52 |
| 2.1 | 1925 | 0.0597 | 27.11 |
| 2.4 | 2200 | 0.0610 | 25.52 |
| 2.7 | 2475 | 0.0609 | 25.64 |
| 3.0 | 2750 | 0.0600 | 26.74 |

TABLE III

| Complex of Example | Amount of Complex (% w) | Conc. of Mo (ppm) | $u_{ref}$ | $u_{comp}$ | Friction Reduction (%) |
|---|---|---|---|---|---|
| 1 | 1.5 | 1680 | 0.0805 | 0.063 | 21.74 |
| 2 | 1.5 | 1020 | 0.0789 | 0.063 | 20.15 |
| 3 | 1.8 | 2395 | 0.0813 | 0.065 | 20.05 |
| 6 | 1.2 | 910 | 0.0840 | 0.060 | 28.57 |
| 7 | 1.2 | 840 | 0.0814 | 0.061 | 25.06 |
| 8 | 1.2 | 610 | 0.0814 | 0.064 | 21.38 |
| 9 | 1.5 | 735 | 0.0805 | 0.065 | 19.25 |
| 10 | 2.4 | 985 | 0.0813 | 0.065 | 20.05 |
| 10 | 2.5 | 1025 | 0.0876 | 0.066 | 24.66 |
| 11 | 1.2 | 660 | 0.0822 | 0.061 | 25.79 |
| 12 | 1.8 | 725 | 0.0809 | 0.062 | 23.36 |
| 13 | 1.2 | 770 | 0.0809 | 0.062 | 23.36 |
| 14 | 1.2 | 900 | 0.0819 | 0.060 | 26.74 |
| 15 | 1.2 | 850 | 0.0865 | 0.061 | 29.48 |
| 16 | 1.2 | 1310 | 0.0815 | 0.064 | 21.47 |
| 17 | 0.9 | 1160 | 0.0791 | 0.062 | 21.62 |
| 18 | 0.9 | 1145 | 0.0807 | 0.062 | 23.17 |
| 19 | 1.2 | 1225 | 0.0817 | 0.063 | 22.89 |
| 20 | 1.2 | 1140 | 0.0802 | 0.067 | 16.46 |
| 21 | 2.1 | 2980 | 0.0812 | 0.062 | 23.65 |
| 22 | 1.5 | 1725 | 0.0820 | 0.062 | 24.39 |
| 35 | 1.5 | 1065 | 0.0911 | 0.057 | 37.43 |
| 36 | 1.5 | 1080 | 0.0815 | 0.064 | 21.47 |

What is claimed is:

1. A molybdenum-containing complex prepared by reacting an alkaline earth metal salt of a carboxylic acid, an amine and a source of cationic molybdenum, wherein the ratio of the number of equivalents of acid groups to the number of moles of molybdenum (eq:mol) is in the range from 1:10 to 10:1, and the ratio of the number of equivalents of acid groups to the number of moles of amine (eq:mol) is in the range from 20:1 to 1:10.

2. A molybdenum-containing complex prepared by reacting a carboxylic acid or metal salt thereof, an amine and a source of cationic molybdenum, wherein the ratio of the number of equivalents of acid groups to the number of moles of molybdenum (eq:mol) is in the range from 1:10 to 10:1, and the ratio of the number of equivalents of acid groups to the number of moles of amine (eq:mol) is in the range from 20:1 to 1:10 wherein the carboxylic acid or metal salt thereof is selected from $C_1$–$C_{24}$ alkyl salicylic acids and alkali metal and alkaline earth metal salts thereof.

3. The complex according to claim 2, wherein the metal salt is a calcium salt.

4. The complex according to claim 1, wherein the amine is a compound of the general formula

  (I)

in which each of $R^1$, $R^2$ and $R^3$ independently represents a hydrogen atom, an alkyl or alkenyl group, optionally substituted by a cycloalkyl group, or a cycloalkyl group optionally substituted by an alkyl or alkenyl group, provided that $R^1$, $R^2$ and $R^3$ do not simultaneously represent a hydrogen atom.

5. The complex according to claim 4, wherein the amine is a mono-, di- or tri($C_4$-alkyl)amine.

6. The complex according to claim 1, wherein the source of cationic molybdenum is an oxide, halide, acid or salt.

7. The complex according to claim 2, wherein the ratio of the number of equivalents of acid groups to the number of moles of molybdenum (eq:mol) is in the range from 1:5 to 5:1.

8. The complex according to claim 2, wherein the ratio of the number of equivalents of acid groups to the number of moles of amine (eq:mol) is in the range from 15:1 to 1:10.

9. The complex according to claim 3, wherein the molybdenum content is in the range from 4 to 8% w, based on the weight of the complex.

* * * * *